US011529357B2

(12) United States Patent
Petersen et al.

(10) Patent No.: US 11,529,357 B2
(45) Date of Patent: Dec. 20, 2022

(54) INJECTABLE CARBAMAZEPINE COMPOSITION ESSENTIALLY FREE OF 10-BROMO-CARBAMAZEPINE

(71) Applicant: H. Lundbeck A/S, Valby (DK)

(72) Inventors: Hans Petersen, Valby (DK); Jesper Tungelund Larsen, Valby (DK)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 16/778,302

(22) Filed: Jan. 31, 2020

(65) Prior Publication Data

US 2020/0276207 A1 Sep. 3, 2020

(30) Foreign Application Priority Data

Feb. 1, 2019 (DK) .............................. PA 201900150
Mar. 15, 2019 (DK) .............................. PA 201900320

(51) Int. Cl.
*A61K 31/55* (2006.01)
*A61K 9/00* (2006.01)
*A61K 47/40* (2006.01)

(52) U.S. Cl.
CPC ............ *A61K 31/55* (2013.01); *A61K 9/0053* (2013.01); *A61K 47/40* (2013.01)

(58) Field of Classification Search
CPC ....... A61K 31/55; A61K 47/40; A61K 9/0019
See application file for complete search history.

(56) References Cited

U.S. PATENT DOCUMENTS

| 5,134,127 | A | 7/1992 | Stella et al. |
| 9,629,797 | B2 | 4/2017 | Cloyd et al. |
| 9,770,407 | B2 | 9/2017 | Cloyd et al. |
| 2007/0104791 | A1* | 5/2007 | Popov .................. A61K 9/0043 424/488 |
| 2010/0204178 | A1 | 8/2010 | Cloyd et al. |

FOREIGN PATENT DOCUMENTS

| EP | 0237952 A1 | 9/1987 |
| GB | 1246606 A | 9/1971 |
| GB | 1495176 A | 12/1977 |
| WO | WO-93/10794 A1 | 6/1993 |
| WO | WO-2007/041524 A3 | 4/2007 |

OTHER PUBLICATIONS

El-Mallakh, R.S., et al., "A blinded, randomized comparison of immediate-release and extended-release carbamazepine capsules in manic and depressed bipolar subjects," Annals of Clinical Psychiatry, vol. 22, No. 1, pp. 3-8 (Feb. 2010).

Vigo, D.V. and Baldessarini, R.J., "Anticonvulsants in the Treatment of Major Depressive Disorder: An Overview," Harv. Rev. Psychiatry, vol. 17, pp. 231-241 (Aug. 2009).

Elphick, Martin, "An Open Clinical Trial of Carbamazepine in Treatment-Resistant Bipolar and Schizo-Affective Psychotics," British Journal of Psychiatry, vol. 147, pp. 198-200 (1985).

Nasrallah, H.A., et al., "Carbamazepine and valproate for the treatment of bipolar disorder: a review of the literature," Journal of Affective Disorders, vol. 95, pp. 69-78 (Jun. 2006).

Yerevanian, B.I., et al., "Bipolar pharmacotherapy and suicidal behavior. Part I: Lithium, divalproex and carbamazepine," Journal of Affective Disorders, vol. 103, pp. 5-11 (Jul. 2007).

British Pharmacopoeia, vol. I, London: Medicines and Healthcare products Regulatory Agency, 2019; Carbamazepine, cover pages, TOC, pp. I-428-1-429 (6 total pages).

Craig, P.N., et al, "Analogs of Phenothiazines. I. 5H-Dibenz[b,f]azepine and Derivatives. A New Isostere of Phenothiazine[1]," A New Isostere of Phenothiazine, vol. 26, pp. 135-138 (Jan. 1961).

Cyr, T.D., et al, "Liquid Chromatographic Methods for Assay of Carbamazepine, 10,11-Dihydrocarbamazepine, and Related Compounds in Carbamazepine Drug Substance and Tablets," J. Assoc. Off. Anal. Chem., vol. 70, No. 5, pp. 836-840, (1987).

Duennbier, U., et al,"Determination of the By-product 10-Bromocarbamazepine in the Drug Carbamazepine by DC Polarography and Differential Pulse Polarography," Pharmazie, vol. 41, Issue 8, pp. 567-570 (1986) with English translation (8 total pages).

Elliott, E.-C., et al, "Convenient Syntheses of Benzo-Fluorinated Dibenz[b,f]azepines: Rearrangements of Isatins, Acridines, and Indoles", Org. Lett., vol. 13, No. 20, pp. 5592-5595 (Sep. 2011).

European Pharmacopoeia, 10th Ed., vol. II, Strasbourg, FR: European Directorate for the Quality of Medicines & Healthcare of the Council of Europe, 2019; Carbamazepine, cover pages, TOC, pp. 2078-2080 (6 total pages).

Evans, D.L., et al., "Nickel Peroxide Dehydrogenation of Oxygen-, Sulfur-, and Nitrogen-Containing Heterocycles", J. Org. Chem., vol. 44, No. 4, pp. 497-501 (1979).

Huisgen, R. et al, "2.3;6.7-Dibenzoazepine," Chem. Berichte., vol. 093, pp. 392-397 (1960) with English translation (12 total pages).

Inoue, M., et al "Catalytic Dehydrogenation of Iminodibenzyl to Iminostilbene on $Mn_2O_3$—$SnO_2$," Chem. Pharm. Bull., vol. 30, No. 1, pp. 24-27 (1982).

Mosher, G. and Thompson, D.O., "Complexation and Cyclodextrins," Encyclopedia of Pharm. Tech., Marcel Dekker Inc., pp. 531-558 (2002).

Schmidt, A.H. and Wess, C., "A QBD With Design-of-Experiments Approach for Development of a State-of-The-Art UPLC Purity Method for Carbamazepine," J. Liq. Chrom. & Rel. Tech., vol. 37, pp. 2653-2666 (2014).

Shamshin, V.P., et al, "Methods of Synthesis and Technology of Drug Production—Synthesis of Carbamazepine and Its Antialcohol Activity," Pharm. Chem. J., vol. 21, pp. 443-448 (1986).

Tokmakov, G.P. and Grandberg, I.I., "Rearrangement of 1-Arylindoles to 5H-Dibenz[b,f]azepines," Tetrahedron, vol. 51, No. 7, pp. 2091-2098 (1995).

(Continued)

*Primary Examiner* — Shobha Kantamneni
(74) *Attorney, Agent, or Firm* — Wilmer Cutler Pickering Hale and Dorr LLP (57) ABSTRACT

An injectable pharmaceutical composition comprising carbamazepine and sulfobutylether-7-β-cyclodextrin, wherein said composition is essentially free of 10-Br-carbamazepine, is disclosed. Methods for the manufacture of said composition and methods for treatment of disease using said composition are also disclosed.

19 Claims, 6 Drawing Sheets

(56) References Cited

OTHER PUBLICATIONS

United States Pharmacopoeia and The National Formulary (USP 42-NF 37), vol. 1, Rockville, MD: The United States Pharmacopeial Convention, 2019; Carbamazepine, cover pages, TOC, pp. 722-729 (13 total pages).

"Carbamazepine", British Pharmacopoeia 2019, vol. 1, available Aug. 1, 2018, effective date Jan. 1, 2019. 7 pages.

"Carbamazepine", European Pharmacopoeia Ninth Edition, vol. 2, Jul. 2016. 5 pages.

"Carbamazepine", The United States Pharmacopeia, vol. 1, May 1, 2018. 22 pages.

International Search Report and Written Opinion dated Jul. 1, 2020, in the International Application No. PCT/EP2020/052391. 10 pages.

ICH Guideline Implementation, Search for the Status of Implementation of ICH Guidelines by ICH Members. First accessed Sep. 16, 2021. 5 pages, (https://www.ich.org/page/ich-guideline-implementation).

ICH Harmonised Tripartite Guideline, "Impurities in New Drug Substances Q3A(R2)," International Conference on Harmonisation of Technical Requirements for Registration of Pharmaceuticals for Human Use, Current Step 4 version, Oct. 25, 2006. 15 pages.

ICH Harmonised Tripartite Guideline, "Specifications: Test Procedures and Acceptance Criteria for New Drug Substances and New Drug Products: Chemical Substances Q6A," International Conference on Harmonisation of Technical Requirements for Registration of Pharmaceuticals for Human Use, Current Step 4 version, Oct. 6, 1999. 35 pages.

Product Details, "Carbamazepine, USP," Spectrum Chemical MFG Corp. First accessed Sep. 19, 2021. 3 pages.

Substances for Pharmaceutical Use, European Pharmacopoeia 6.0, Jan. 2008, pp. 703-705.

* cited by examiner

INJECTABLE CARBAMAZEPINE COMPOSITION ESSENTIALLY FREE OF 10-BROMO-CARBAMAZEPINE

This application claims priority to Denmark Application Nos. PA201900320, filed Mar. 15, 2019, and PA201900150, filed Feb. 1, 2019, the contents of which are hereby incorporated by reference in their entireties.

FIELD OF THE INVENTION

The present invention provides an injectable pharmaceutical composition comprising carbamazepine and a sulfoalkyl-cyclodextrin wherein said composition is essentially free of 10-Br-carbamazepine, a process for the manufacture of said composition, and a therapeutic use of said composition.

BACKGROUND OF THE INVENTION

Throughout this application, various publications are referenced in full. The disclosures of these publications are hereby incorporated by reference, in their entireties, into this application to describe more fully the state of the art to which this invention pertains.

Carbamazepine is a well-established psychotropic drug which received its first approval for the treatment of trigeminal neuralgia in 1962. Carbamazepine was approved in 1974 in the U.S. as an anticonvulsant and antiepileptic and has since developed to be a first-line treatment for seizures, including partial seizures with complex symptomatology, generalized tonic-clonic seizures (grand mal), and partial and generalized seizures. Carbamazepine is also approved for acute manic or mixed episodes associated with bipolar disorder and trigeminal neuralgia. Carbamazepine is sold, e.g., under the tradenames Tegretol™, Carbatrol™, and Equetro™. These carbamazepine products are all intended for oral administration, e.g., in the form of instant release tablets, modified release tablets, or oral suspensions. Carbamazepine is dosed orally, initially at 200 mg twice daily, with a maintenance dose between 1200 and 1600 mg dosed 3-4 times daily across approved indications. Carbamazepine has also shown effect in, e.g., mania, bipolar depression, and major depressive disorder. See, e.g., *Annal. Clin. Psych.* 22, 3-8, 2010; *Harv. Rev. Psych.* 17, 231-241, 2009; *J. Affect. Dis.* 95, 69-78, 2006; *J. Affect. Dis.* 103, 5-11, 2007; and *Br. J. Psych.* 147, 198-200, 1985 (each hereby incorporated by reference in its entirety).

In addition to its established efficacy, carbamazepine also has a favorable safety profile. For instance, carbamazepine is less sedating and causes less impairment of intellectual functions compared to other anticonvulsants, properties which have induced its wide-spread use.

Carbamazepine is not available in a parenteral formulation, which is a problem for patients unable to take medicine orally. These patient subgroups include, e.g., patients undergoing surgery, patients with gastro-intestinal diseases, and patients unable to swallow, e.g., due to seizures or unconsciousness. Due to the high-frequency dosing and the relatively fast metabolism of carbamazepine, patients unable to take carbamazepine orally will quickly reach a sub-clinical carbamazepine plasma level, which may induce potentially life-threatening seizures.

To be able to offer certain carbamazepine patients who are unable to take their medication orally an alternative treatment, an injectable composition has been developed comprising carbamazepine and a sulfoalkyl cyclodextrin, sulfobutylether-7-β-cyclodextrin. See U.S. Pat. Nos. 9,629,797 and 9,770,407 (each hereby incorporated by reference in its entirety). In October 2016, the U.S. Food and Drug Administration ("FDA") approved such a product under the tradename Carnexiv™ as replacement therapy for oral carbamazepine when oral administration is temporarily unfeasible, and where the total daily dose of carbamazepine is reduced to 70% of the total oral dose. Carnexiv™ is indicated for
  partial seizures with complex symptomatology;
  generalized tonic-clonic seizures; and
  mixed seizures patterns which include the above, or other partial or generalized seizures.

Carnexiv™ is administered by intravenous (IV) infusions. Carnexiv™ was, however, never commercialized due to the identification of visible precipitate in the product when manufactured at the commercial scale, meaning it did not meet FDA regulatory specifications. The marketing status of Carnexiv™ is "Discontinued" (see Drugs@FDA database entry for "Carnexiv").

The present invention aims at providing a composition comprising carbamazepine and sulfobutylether-7-β-cyclodextrin essentially free of visible precipitate and thus useful, e.g., as a replacement therapy for oral carbamazepine.

SUMMARY OF THE INVENTION

The present inventors have surprisingly found that the visible precipitate identified in compositions comprising carbamazepine and sulfobutylether-7-β-cyclodextrin is caused by trace amounts of 10-Br-carbamazepine. Accordingly, in one aspect, the present invention provides an injectable pharmaceutical composition comprising carbamazepine and sulfobutylether-7-β-cyclodextrin, wherein said composition is essentially free of 10-Br-carbamazepine.

In another aspect, the invention provides an injectable pharmaceutical composition comprising carbamazepine and sulfobutylether-7-β-cyclodextrin, wherein said carbamazepine is obtained in a manufacturing process that achieves essentially no 10-Br-carbamazepine as a by-product.

In yet another aspect, the invention provides a process for the manufacture of an injectable pharmaceutical composition comprising carbamazepine, from a batch of carbamazepine, and sulfobutylether-7-β-cyclodextrin, which process comprises the steps of:
  a) analyzing said batch of carbamazepine for its content of 10-Br-carbamazepine, and
  b) discharging said batch if said batch is not essentially free of 10-Br-carbamazepine.

In still another aspect, the invention provides a process for the manufacture of an injectable pharmaceutical composition comprising carbamazepine, from a batch of carbamazepine, and sulfobutylether-7-β-cyclodextrin, which process comprises the steps of:
  a) analyzing said batch of carbamazepine for its content of 10-Br-carbamazepine, and
  b) subjecting said batch of carbamazepine to a purification step to reduce its content of 10-Br-carbamazepine if said batch is not essentially free of 10-Br-carbamazepine.

In still another aspect, the invention provides a process for the manufacture of an injectable pharmaceutical composition comprising carbamazepine and sulfobutylether-7-β-cyclodextrin, wherein said carbamazepine is manufactured in a process that achieves carbamazepine essentially free of 10-Br-carbamazepine.

In still another aspect, the invention provides for a process for the manufacture of an injectable pharmaceutical composition comprising carbamazepine and sulfobutylether-7-β-cyclodextrin comprising mixing carbamazepine, sulfobutylether-7-β-cyclodextrin, and water, wherein said carbamazepine is obtained from a manufacturing process that achieves essentially no 10-Br-carbamazepine.

In still another aspect, the invention provides a method for treatment of a disease selected from seizures, mania, bipolar depression, mixed episodes, major depressive disorder or trigeminal neuralgia, the method comprising the administration of a therapeutically effective amount of an injectable pharmaceutical composition of the present invention to a patient in need thereof.

In still another aspect, the invention provides the use of an injectable pharmaceutical composition of the present invention in the manufacture of a medicament for the treatment of a disease selected from seizures, mania, bipolar depression, mixed episodes, major depressive disorder, or trigeminal neuralgia.

In still another aspect, the invention provides an injectable pharmaceutical composition of the present invention for use in the treatment of a disease selected from seizures, mania, bipolar depression, mixed episodes, major depressive disorder, or trigeminal neuralgia.

DETAILED DESCRIPTION OF THE INVENTION

Carbamazepine has the chemical name 5H-dibenzo[b,f]azepine-5-carboxamide, and the molecular structure

As mentioned above, it has wide-spread use as an anticonvulsant, i.e., for the treatment of seizures. It is believed that the clinical effect of carbamazepine is mainly explained by its activity as voltage-dependent sodium-channel blocker, prolonging the inactive state of the sodium-channel. Carbamazepine is on the World Health Organization's Model List of Essential Medicines.

Carnexiv™ is an injectable pharmaceutical composition of carbamazepine and sulfobutylether-7-β-cyclodextrin. It comprises 10 mg/mL carbamazepine, 250 mg/mL sulfobutylether-7-β-cyclodextrin sodium, and 0.78 mg/mL phosphate monobasic dihydrate and water for injection. pH is adjusted to 6.2 with NaOH or HCl as needed. Carnexiv™ is supplied in a 20 mL vial which is diluted with 100 mL diluent solution (e.g. 0.9% NaCl) prior to IV infusion, which takes place over approximately 30 minutes. Larger or smaller volumes of Carnexiv™ may be diluted to adjust for the dose needed in a particular patient. Dose frequency is about 6 hours, and the total daily dose is 70% of the oral dose.

Cyclodextrins are cyclic oligosaccharides with hydroxyl groups on the outer surface and a cavity in the middle. Cyclodextrins with seven 1 to 4 linked α-D-glucopyranoside subunits are known as β-cyclodextrin. Owing to the hydrophilic exterior, cyclodextrins are water soluble whereas the cavity has hydrophobic properties. Cyclodextrins may form complexes with a hydrophobic compound (guest molecule) which is fully or partly contained in the cavity of the cyclodextrin molecule, often resulting in a marked increase in the aqueous solubility of the hydrophobic compound. Various chemical modifications of cyclodextrins are known aiming at modifying the properties of the cyclodextrin (see *Encyclopedia of Pharmaceutical Technology*, page 531-538, Marcel Dekker, 2002; hereby incorporated by reference in its entirety). In particular, sulfoalkyl ether β-cyclodextrins are known, i.e., cyclodextrins functionalized with, e.g., ($C_2$-$C_6$-alkylene)-$SO_3^-$ groups (see U.S. Pat. No. 5,134,127; hereby incorporated by reference in its entirety). A sulfoalkyl ether cyclodextrin is typically ionized at physiological pH and is therefore accompanied by a counter ion, such as $Na^+$. Sulfoalkyl ether β-cyclodextrin with approximately seven sulfobutyl ether groups per cyclodextrin molecule is referred to as sulfobutylether-7-β-cyclodextrin. The sodium salt of sulfobutylether-7-β-cyclodextrin is also known as betadex sulfobutyl ether sodium and is, e.g., sold under the tradename Captisol™.

Carnexiv™ may be manufactured by mixing carbamazepine, sulfobutylether-7-β-cyclodextrin sodium, and sodium phosphate monobasic dihydrate and water for injection. At industrial or commercial scale, for example, 10 kg carbamazepine is mixed with 0.78 kg sodium phosphate monobasic dihydrate and 250 kg sulfobutylether-7-β-cyclodextrin sodium in approximately 1000 L water for injection. After mixing, the pH is adjusted to 6.2 with NaOH or HCl as needed. Due to the sterile requirement for pharmaceutical products intended for IV administration, the solution may be sterile filtered, e.g., through one or more 0.22 μm filter(s), followed by aseptic filling and terminal sterilization, e.g., autoclaving at 121° C. for 30 minutes.

10-Br-carbamazepine (10-bromo-5H-dibenzo[b,f]azepine-5-carboxamide) has the chemical structure 10-Br-carbamazepine was disclosed in GB 1495176 (herein incorporated by reference in its entirety), which published in 1977, and was claimed to have prolonged anticonvulsive action.

Figure 1:
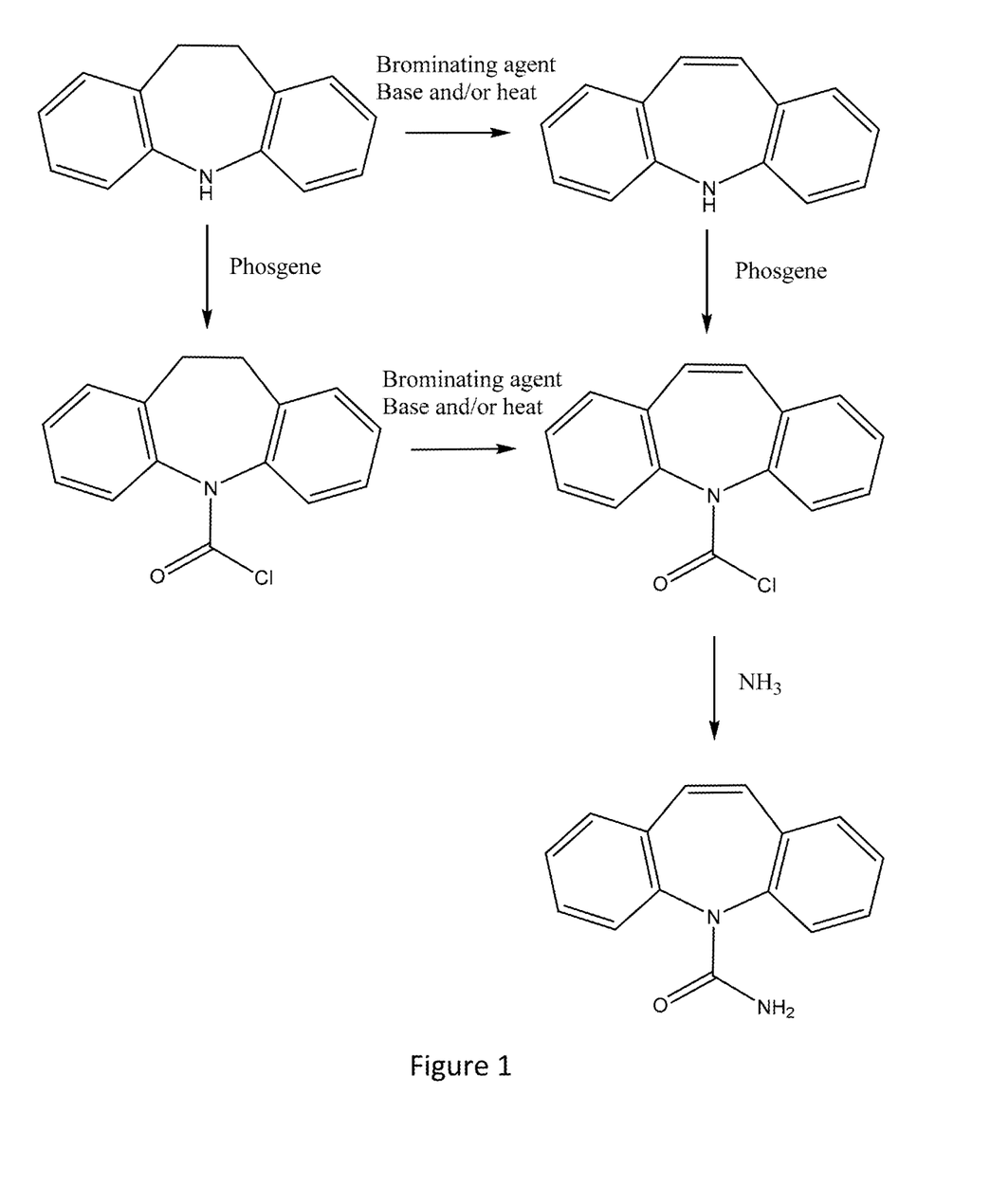
FIG. 1: Manufacturing route for carbamazepine.

10-Br-carbamazepine may be found in carbamazepine active pharmaceutical ingredient ("API") as a manufacturing process by-product. 10,11-Dihydro-5H-dibenzo[b,f]azepine (iminodibenzyl) is a typical starting point for carbamazepine manufacture, which may be reacted with phosgene to achieve 5-chlorocarbonyl-iminodibenzyl. This intermediate is further reacted with a brominating agent (e.g., $Br_2$ or N-bromosuccinimide) to achieve a mixture of 10-Br-5-chlorocarbonyl-iminodibenzyl and 10,11-dibromo-5-chlorocarbonyl-iminodibenzyl. Thermal debromination and dehydrobromination followed by treatment with ammonia achieve carbamazepine. Alternatively, iminodibenzyl may be treated with a brominating agent (e.g., $Br_2$ or N-bromosuccinimide) in an initial step followed by thermal debromination and dehydrobromination, treatment with phosgene, and treatment with ammonia to achieve carbamazepine (see FIG. 1). Alternatives to the use of phosgene exist—see, e.g., Example 4. Unwanted side-reactions, e.g., dehydrobromination of 10,11-dibromo-5-chlorocarbonyl-iminodibenzyl or 10,11-dibromo-iminodibenzyl, may result in the formation of 10-Br-carbamazepine. The by-product 10-Br-carbamazepine may be removed or reduced, e.g., in a recrystallization step, e.g., from ethanol (see *Pharmazie* 41, 567-570, 1986; GB 1246606; and *Pharm. Chem. J.*, 21, 443-448, 1986 (each hereby incorporated by reference in its entirety)). Analytical data disclosed in *J. Assoc. Off. Anal. Chem.* 70, 836-840, 1987 (hereby incorporated by reference in its entirety) shows that 10-Br-carbamazepine is a common impurity in commercial carbamazepine API and tablets at a level which is significant in the context of the present invention.

The British and the European Pharmacopeia for carbamazepine recognize 10-Br-carbamazepine as one of seven impurities and recommend testing for 10-Br-carbamazepine (Impurity G) depending on the synthetic route. 10-Br-carbamazepine is not identified as a "specified impurity", and, accordingly, up to 0.1% (1000 ppm relative to carbamazepine, i.e., 0.001 g per g) is accepted. The total amount of impurities cannot exceed 0.5% (5000 ppm relative to carbamazepine).

The U.S. Pharmacopeia does not recognize 10-Br-carbamazepine as an impurity (carbamazepine related compound). The acceptance limit is thus 0.2% (2000 ppm relative to carbamazepine) with total impurity limit of 0.5% (5000 ppm relative to carbamazepine).

As mentioned above, visible particulates were discovered in commercial batches of Carnexiv™ which ultimately kept the product off the market. The present inventors carried out investigations and have surprisingly found that an impurity often found in batches of carbamazepine API causes the particulate formation. The impurity, 10-Br-carbamazepine, is present only in trace amounts, i.e., well below the acceptable limits identified by the British, European, and U.S. Pharmacopeias, and its presence is the result of the manufacturing route. As shown in Example 1, visible particulates isolated from Carnexiv™ batches after three months of storage have an infrared (IR) spectrum consistent with a carbamazepine analogue. Moreover, analyses using scanning electron microscopy with energy dispersive X-ray spectrometry (SEM/EDS) revealed that the particulates contain nitrogen and elevated levels of bromine. EDS is an analytical technique in which an X-ray is directed towards the sample to be analyzed. The X-ray excites an electron from an inner electron shell and the resulting electron hole is filled with an electron from an outer shell. This is accompanied by X-ray emission, and the energy of the emitted X-rays reflects the identity of, and the intensity of emitted radiation reflects the amount of, elements present in the sample. EDS can therefore be used for quantitative elemental analysis. Coupled with SEM, it is a powerful tool for such analysis in small particles.

The data obtained in Example 2 confirms the finding of Example 1. Vials from one of the Carnexiv™ batches from Example 1 was analyzed after 12 months of storage. The IR spectrum obtained from isolated particulates is consistent with a carbamazepine analogue and SEM/EDS shows the presence of nitrogen and elevated levels of bromine.

The data obtained in Example 3 show that the carbamazepine batch used in the preparation of the Carnexiv™ batches analyzed in Examples 1 and 2 contains approximately 80-60 ppm 10-Br-carbamazepine. The data also show that the carbamazepine batch used to prepare an injectable pharmaceutical composition of the present invention which is analyzed in Example 4 is essentially free of 10-Br-carbamazepine.

The data presented in Example 4 shows that particulates isolated from an injectable pharmaceutical composition of the present invention prepared from a batch of carbamazepine essentially free of 10-Br-carbamazepine do not have an IR spectrum that can reasonably be assigned to a carbamazepine and that said particles do not contain bromine. The particles that were isolated were identified as environmental debris caused by the fact that the batch analyzed was prepared in a non-sterile development laboratory, i.e., under environmental requirements much less stringent than those for pharmaceutical production. It is therefore to be expected that such samples may contain cellulose fibres, plastic particles, glass particles, etc., which may be found when analyzing samples with SEM/EDS apparatus.

Example 5 discloses 3-month stability data from two batches of Carnexiv™ prepared at commercial scale using carbamazepine manufactured in the same manner as the carbamazepine used in Example 4, i.e., essentially free of 10-Br-carbamazepine. The data show that the vials were clear and free from visible particulates after three months of storage under accelerated conditions.

The data in Examples 4 and 5 support the inventors' hypothesis that the precipitate observed in Examples 1 and 2, and which prevented marketing of Carnexiv™, is caused by trace amounts of 10-Br-carbamazepine, which was previously unknown in the art. Accordingly, the data presented in the examples makes it reasonable to conclude that a batch of carbamazepine should preferably contain less than about 60 ppm 10-Br-carbamazepine relative to carbamazepine in order to avoid formation of particulates if said batch of carbamazepine is used to prepare an injectable pharmaceutical composition comprising carbamazepine and sulfobutylether-7-β-cyclodextrin.

In one aspect, the invention provides an injectable pharmaceutical composition comprising carbamazepine and sulfobutylether-7-β-cyclodextrin, wherein said composition is essentially free of 10-Br-carbamazepine. In some embodiments, said composition also comprises water, such as water for injection. In the present context, "essentially free" is intended to indicate that said composition comprises less than about 60 ppm, such as less than about 50 ppm, such as less than about 40 ppm, such as less than about 30 ppm, such as less than about 20 ppm, or such as less than about 10 ppm 10-Br-carbamazepine relative to carbamazepine. In some embodiments, said composition comprises less than about 60 ppm 10-Br-carbamazepine relative to carbamazepine. In some embodiments, said composition comprises less than about 50 ppm 10-Br-carbamazepine relative to carbamazepine. In some embodiments, said composition comprises less than about 40 ppm 10-Br-carbamazepine relative to carbamazepine. In some embodiments, said composition comprises less than about 30 ppm 10-Br-carbamazepine relative to carbamazepine. In some embodiments, said composition comprises less than about 20 ppm 10-Br-carbamazepine relative to carbamazepine. In some embodiments, said composition comprises less than about 10 ppm 10-Br-carbamazepine relative to carbamazepine. In some embodiments, said composition comprises about 5-15 mg/mL carbamazepine, such as about 10 mg/mL carbamazepine. In some embodiments, said composition comprises about 10 mg/mL carbamazepine. In some embodiments, said composition comprises about 200-300 mg/mL sulfobutylether-7-β-cyclodextrin sodium, such as about 250 mg/mL sulfobutylether-7-β-cyclodextrin sodium. In some embodiments, said composition comprises about 250 mg/mL sulfobutylether-7-β-cyclodextrin sodium. In some embodiments, said composition comprises about 10 mg/mL carbamazepine and about 250 mg/mL sulfobutylether-7-β-cyclodextrin sodium. An injectable pharmaceutical composition typically has a pH near physiological pH. Thus, in some embodiments, said composition is buffered, e.g., with a phosphate buffer, acetate buffer, or citrate buffer to achieve a pH between about 5.5 and 7.5, such as about 6.2. Buffering may be achieved, e.g., by addition of about 0.4-1.5 mg/mL, such as about 0.5-1.0 mg/mL, such as about 0.78 mg/mL, sodium phosphate monobasic dihydrate to said composition and adjusting pH to about 6.2 using NaOH or HCl as required. In some embodiments, said composition is sterile.

In some embodiments, said composition comprises about 10 mg/mL carbamazepine, about 250 mg/mL sulfobutylether-7-β-cyclodextrin sodium, about 0.78 mg/mL sodium phosphate monobasic dihydrate, and water for injection, having pH about 6.2 and comprising less than about 60 ppm, such as less than about 50 ppm, such as less than about 40 ppm, such as less than about 30 ppm, such as less than about 20 ppm, or such as less than about 10 ppm 10-Br-carbamazepine relative to carbamazepine. In some embodiments, said composition comprises about 10 mg/mL carbamazepine, about 250 mg/mL sulfobutylether-7-β-cyclodextrin sodium, about 0.78 mg/mL sodium phosphate monobasic dihydrate, and water for injection, having pH about 6.2 and comprising less than about 60 ppm 10-Br-carbamazepine relative to carbamazepine. In some embodiments, said composition comprises about 10 mg/mL carbamazepine, about 250 mg/mL sulfobutylether-7-β-cyclodextrin sodium, about 0.78 mg/mL sodium phosphate monobasic dihydrate, and water for injection, having pH about 6.2 and comprising less than about 50 ppm 10-Br-carbamazepine relative to carbamazepine. In some embodiments, said composition comprises about 10 mg/mL carbamazepine, about 250 mg/mL sulfobutylether-7-β-cyclodextrin sodium, about 0.78 mg/mL sodium phosphate monobasic dihydrate, and water for injection, having pH about 6.2 and comprising less than about 40 ppm 10-Br-carbamazepine relative to carbamazepine. In some embodiments, said composition comprises about 10 mg/mL carbamazepine, about 250 mg/mL sulfobutylether-7-β-cyclodextrin sodium, about 0.78 mg/mL sodium phosphate monobasic dihydrate, and water for injection, having pH about 6.2 and comprising less than about 30 ppm 10-Br-carbamazepine relative to carbamazepine. In some embodiments, said composition comprises about 10 mg/mL carbamazepine, about 250 mg/mL sulfobutylether-7-β-cyclodextrin sodium, about 0.78 mg/mL sodium phosphate monobasic dihydrate, and water for injection, having pH about 6.2 and comprising less than about 20 ppm 10-Br-carbamazepine relative to carbamazepine. In some embodiments, said composition comprises about 10 mg/mL carbamazepine, about 250 mg/mL sulfobutylether-7-β-cyclodextrin sodium, about 0.78 mg/mL sodium phosphate monobasic dihydrate, and water for injection, having pH about 6.2 and comprising less than about 10 ppm 10-Br-carbamazepine relative to carbamazepine.

The present invention discloses the manufacture of an injectable pharmaceutical composition comprising carbamazepine and sulfobutylether-7-β-cyclodextrin, wherein said carbamazepine is essentially free of 10-Br-carbamazepine. Thus, in another aspect, the invention provides a process for the manufacture of an injectable pharmaceutical composition comprising carbamazepine, from a batch of carbamazepine, and sulfobutylether-7-β-cyclodextrin, the process comprising the steps of:
 a. analyzing said batch of carbamazepine for its content of 10-Br-carbamazepine, and
 b. discharging said batch if said batch is not essentially free of 10-Br-carbamazepine.

In some embodiments, the method of analyzing said batch of carbamazepine for content of 10-Br-carbamazepine (step a) comprises chromatography, such as a form of liquid chromatography or HPLC. In some embodiments, the method of analyzing said batch of carbamazepine for content of 10-Br-carbamazepine comprises electrochemical analysis, such as differential pulse polarography. In some embodiments, said composition also comprises water, such as water for injection. In some embodiments, said batch is discharged if it contains more than about 60 ppm, such as more than about 50 ppm, such as more than about 40 ppm, such as more than about 30 ppm, such as more than about 20 ppm, or such as more than about 10 ppm 10-Br-carbamazepine relative to carbamazepine. In some embodiments, said batch is discharged if it contains more than about 60 ppm 10-Br-carbamazepine relative to carbamazepine. In some embodiments, said batch is discharged if it contains more than about 50 ppm 10-Br-carbamazepine relative to carbamazepine. In some embodiments, said batch is discharged if it contains more than about 40 ppm 10-Br-carbamazepine relative to carbamazepine. In some embodiments, said batch is discharged if it contains more than about 30 ppm 10-Br-carbamazepine relative to carbamazepine. In some embodiments, said batch is discharged if it contains more than about 20 ppm 10-Br-carbamazepine relative to carbamazepine. In some embodiments, said batch is discharged if it contains more than about 10 ppm 10-Br-carbamazepine relative to carbamazepine.

In some embodiments, said process is for the manufacture of an injectable pharmaceutical composition comprising about 5-15 mg/mL carbamazepine, such as about 10 mg/mL carbamazepine. In some embodiments, said composition comprises about 200-300 mg/mL sulfobutylether-7-β-cyclodextrin sodium, such as about 250 mg/mL sulfobutylether-7-β-cyclodextrin sodium. An injectable pharmaceutical composition typically has a pH near physiological pH. Thus, in some embodiments, said composition is buffered, e.g., with a phosphate buffer, acetate buffer, or citrate buffer to achieve a pH between about 5.5 and 7.5, such as around 6.2. Buffering may be achieved, e.g., by addition of about 0.4-1.5 mg/mL, such as about 0.5-1.0 mg/mL, or such as about 0.78 mg/mL sodium phosphate monobasic dihydrate to said composition and adjusting the pH to about 6.2 using NaOH or HCl as required.

In some embodiments, said process is for the manufacture of an injectable pharmaceutical composition comprising about 10 mg/mL carbamazepine, about 250 mg/mL sulfobutylether-7-β-cyclodextrin sodium, about 0.78 mg/mL sodium phosphate monobasic dihydrate, and water for injection, having pH about 6.2 and comprising less than about 60 ppm, such as less than about 50 ppm, such as less than about 40 ppm, such as less than about 30 ppm, such as less than about 20 ppm, or such as less than about 10 ppm 10-Br-carbamazepine relative to carbamazepine. In some embodiments, said process is for the manufacture of an injectable pharmaceutical composition comprising about 10 mg/mL carbamazepine, about 250 mg/mL sulfobutylether-7-β-cyclodextrin sodium, about 0.78 mg/mL sodium phosphate monobasic dihydrate, and water for injection, having pH about 6.2 and comprising less than about 60 ppm 10-Br-carbamazepine relative to carbamazepine. In some embodiments, said process is for the manufacture of an injectable pharmaceutical composition comprising about 10 mg/mL carbamazepine, about 250 mg/mL sulfobutylether-7-β-cyclodextrin sodium, about 0.78 mg/mL sodium phosphate monobasic dihydrate, and water for injection, having pH about 6.2 and comprising less than about 50 ppm 10-Br-carbamazepine relative to carbamazepine. In some embodiments, said process is for the manufacture of an injectable pharmaceutical composition comprising about 10 mg/mL carbamazepine, about 250 mg/mL sulfobutylether-7-β-cyclodextrin sodium, about 0.78 mg/mL sodium phosphate monobasic dihydrate, and water for injection, having pH about 6.2 and comprising less than about 40 ppm 10-Br-carbamazepine relative to carbamazepine. In some embodiments, said process is for the manufacture of an injectable pharmaceutical composition comprising about 10 mg/mL carbamazepine, about 250 mg/mL sulfobutylether-7-β-cyclodextrin sodium, about 0.78 mg/mL sodium phosphate monobasic dihydrate, and water for injection, having pH about 6.2 and comprising less than about 30 ppm 10-Br-carbamazepine relative to carbamazepine. In some embodiments, said process is for the manufacture of an injectable pharmaceutical composition comprising about 10 mg/mL carbamazepine, about 250 mg/mL sulfobutylether-7-β-cyclodextrin sodium, about 0.78 mg/mL sodium phosphate monobasic dihydrate, and water for injection, having pH about 6.2 and comprising less than about 20 ppm 10-Br-carbamazepine relative to carbamazepine. In some embodiments, said process is for the manufacture of an injectable pharmaceutical composition comprising about 10 mg/mL carbamazepine, about 250 mg/mL sulfobutylether-7-β-cyclodextrin sodium, about 0.78 mg/mL sodium phosphate monobasic dihydrate, and water for injection, having pH about 6.2 and comprising less than about 10 ppm 10-Br-carbamazepine relative to carbamazepine.

As an economically viable alternative to discharging a batch of carbamazepine containing excess amounts of 10-Br-carbamazepine, said batch may be reworked or subjected to a purification step to reduce its content of 10-Br-carbamazepine. Accordingly, in still another aspect, the invention provides a process for the manufacture of an injectable pharmaceutical composition comprising carbamazepine, from a batch of carbamazepine, and sulfobutylether-7-β-cyclodextrin, the process comprising the steps of:
  a. analyzing said batch of carbamazepine for its content of 10-Br-carbamazepine, and
  b. subjecting said batch to a purification step to reduce the content of 10-Br-carbamazepine if said batch is not essentially free of 10-Br-carbamazepine.

In some embodiments, the method of analyzing said batch of carbamazepine for content of 10-Br-carbamazepine (step a) comprises chromatography, such as a form of liquid chromatography or HPLC. In some embodiments, the method of analyzing said batch of carbamazepine for content of 10-Br-carbamazepine comprises electrochemical analysis, such as differential pulse polarography. In some embodiments, said composition also comprises water, such as water for injection. In some embodiments, said batch is subjected to said purification step if it contains more than about 60 ppm, such as more than about 50 ppm, such as more than about 40 ppm, such as more than about 30 ppm, such as more than about 20 ppm, or such as more than about 10 ppm 10-Br-carbamazepine relative to carbamazepine. In some embodiments, said batch is subjected to said purification step if it contains more than about 60 ppm 10-Br-carbamazepine relative to carbamazepine. In some embodiments, said batch is subjected to said purification step if it contains more than about 50 ppm 10-Br-carbamazepine relative to carbamazepine. In some embodiments, said batch is subjected to said purification step if it contains more than about 40 ppm 10-Br-carbamazepine relative to carbamazepine. In some embodiments, said batch is subjected to said purification step if it contains more than about 30 ppm 10-Br-carbamazepine relative to carbamazepine. In some embodiments, said batch is subjected to said purification step if it contains more than about 20 ppm 10-Br-carbamazepine relative to carbamazepine. In some embodiments, said batch is subjected to said purification step if it contains more than about 10 ppm 10-Br-carbamazepine relative to carbamazepine.

In some embodiments, said process is for the manufacture of an injectable pharmaceutical composition comprising about 5-15 mg/mL carbamazepine, such as about 10 mg/mL carbamazepine. In some embodiments, said composition comprises about 200-300 mg/mL sulfobutylether-7-β-cyclodextrin sodium, such as about 250 mg/mL sulfobutylether-7-β-cyclodextrin sodium. An injectable pharmaceutical composition typically has a pH near physiological pH. Thus, in some embodiments, said composition is buffered, e.g., with a phosphate buffer, acetate buffer, or citrate buffer to achieve a pH between about 5.5 and 7.5, such as about 6.2. Buffering may be achieved, e.g., by addition of about 0.4-1.5 mg/mL, such as about 0.5-1.0 mg/mL, or such as about 0.78 mg/mL sodium phosphate monobasic dihydrate to said composition and adjusting pH to about 6.2 using NaOH or HCl as required.

In some embodiments, said process is for the manufacture of an injectable pharmaceutical composition comprising about 10 mg/mL carbamazepine, about 250 mg/mL sulfobutylether-7-β-cyclodextrin sodium, about 0.78 mg/mL sodium phosphate monobasic dihydrate, and water for injection, having pH about 6.2 and comprising less than about 60 ppm, such as less than about 50 ppm, such as less than about 40 ppm, such as less than about 30 ppm, such as less than about 20 ppm, or such as less than about 10 ppm 10-Br-carbamazepine relative to carbamazepine. In some embodiments, said process is for the manufacture of an injectable pharmaceutical composition comprising about 10 mg/mL carbamazepine, about 250 mg/mL sulfobutylether-7-β-cyclodextrin sodium, about 0.78 mg/mL sodium phosphate monobasic dihydrate, and water for injection, having pH about 6.2 and comprising less than about 60 ppm 10-Br-carbamazepine relative to carbamazepine. In some embodiments, said process is for the manufacture of an injectable pharmaceutical composition comprising about 10 mg/mL carbamazepine, about 250 mg/mL sulfobutylether-7-β-cyclodextrin sodium, about 0.78 mg/mL sodium phosphate monobasic dihydrate, and water for injection, having pH about 6.2 and comprising less than about 50 ppm 10-Br-carbamazepine relative to carbamazepine. In some embodiments, said process is for the manufacture of an injectable pharmaceutical composition comprising about 10 mg/mL carbamazepine, about 250 mg/mL sulfobutylether-7-β-cyclodextrin sodium, about 0.78 mg/mL sodium phosphate monobasic dihydrate, and water for injection, having pH about 6.2 and comprising less than about 40 ppm 10-Brcarbamazepine relative to carbamazepine. In some embodiments, said process is for the manufacture of an injectable pharmaceutical composition comprising about 10 mg/mL carbamazepine, about 250 mg/mL sulfobutylether-7-β-cyclodextrin sodium, about 0.78 mg/mL sodium phosphate monobasic dihydrate, and water for injection, having pH about 6.2 and comprising less than about 30 ppm 10-Br-carbamazepine relative to carbamazepine. In some embodiments, said process is for the manufacture of an injectable pharmaceutical composition comprising about 10 mg/mL carbamazepine, about 250 mg/mL sulfobutylether-7-β-cyclodextrin sodium, about 0.78 mg/mL sodium phosphate monobasic dihydrate, and water for injection, having pH about 6.2 and comprising less than about 20 ppm 10-Br-carbamazepine relative to carbamazepine. In some embodiments, said process is for the manufacture of an injectable pharmaceutical composition comprising about 10 mg/mL carbamazepine, about 250 mg/mL sulfobutylether-7-β-cyclodextrin sodium, about 0.78 mg/mL sodium phosphate monobasic dihydrate, and water for injection, having pH about 6.2 and comprising less than about 10 ppm 10-Br-carbamazepine relative to carbamazepine.

In some embodiments, said purification step comprises re-crystallization, including treatment with activated charcoal of said carbamazepine batch, e.g., from ethanol (see *Pharm. Chem. J.*, 21, 443-448, 1998; hereby incorporated by reference in its entirety) or water-methanol (see GB 1246606; hereby incorporated by reference in its entirety). As an example, carbamazepine may be dissolved in ethanol (e.g., approximately 4 mL ethanol per g carbamazepine) by heating in a vessel equipped with reflux condenser, addition of activated charcoal, removal of activated charcoal by filtration, cooling, and collection of the precipitate, i.e., purified carbamazepine.

Alternatively, in some embodiments, a batch of carbamazepine may be subjected to a purification step comprising a chromatography, e.g., chromatography using a reversed-phase column.

Several ways of analysing a batch of carbamazepine or an injectable pharmaceutical composition comprising carbamazepine for its content of 10-Br-carbamazepine are known in the art. The European Pharmacopeia (hereby incorporated by reference in its entirety) discloses a liquid chromatography method using a 250 mm×4.6 mm column with 10 μm nitrile silica gel as the stationary phase. The mobile phase is tetrahydrofuran, methanol, and water (3:12:85 v/v/v) to which is added 0.2 mL formic acid and 0.5 mL triethylamine per 1000 mL. Flow rate is 2 mL/min; UV detection at 230 nm. *J. Assoc. Off. Anal. Chem.* 70, 836-840, 1987 (hereby incorporated by reference in its entirety) disclosed an alternative liquid chromatography method using a 250 mm×4.6 mm column with 5 μm diol bonded column material. The mobile phase is acetonitrile, methanol, and acetic acid (0.05% in water (v/v) (5/5/90 v/v/v). Flow rate is 1 mL/min; UV detection at 230 nm. More recently, *J. Liq. Chrom. & Rel. Tech.* 37, 2653-2666, 2014 (hereby incorporated by reference in its entirety) reported on a development program to improve chromatographic methods for analysis of carbamazepine and structurally related compounds, recommending the use of a 100 mm×2.1 mm column packed with a 1.7 μm C18 reversed phase stationary phase. The mobile phase is 0.2% phosphoric acid with an acetonitrile gradient from 10% to 85% and a temperature of 60° C. UV detection at 230 nm. *Pharmazie*, 41, 567-570, 1986 (hereby incorporated by reference in its entirety) disclosed the use of electrochemical analysis, e.g., differential pulse polarography at a dropping mercury electrode. Example 3 discloses an applicable analytical setup for determination of 10-Br-carbamazepine in a batch of carbamazepine or in a liquid formulation comprising carbamazepine.

In some embodiments, the carbamazepine used to prepare the injectable liquid formulation of the present invention is manufactured in a process which achieves essentially no 10-Br-carbamazepine as a by-product. As described above, 10-Br-carbamazepine may be generated if the double-bond in the 7-membered ring of carbamazepine is generated by bromination and subsequent de-bromination of a single-bond.

In still another aspect, the present invention provides an injectable pharmaceutical composition comprising carbamazepine and sulfobutylether-7-β-cyclodextrin, wherein said carbamazepine in manufactured in a process that achieves essentially no 10-Br-carbamazepine. In some embodiments, said composition also comprises water, such as water for injection. In some embodiments, said process achieves less than about 60 ppm, such as less than about 50 ppm, such as less than about 40 ppm, such as less than about 30 ppm, such as less than about 20 ppm, or such as less than about 10 ppm 10-Br-carbamazepine relative to carbamazepine. In some embodiments, said process achieves less than about 60 ppm 10-Br-carbamazepine relative to carbamazepine. In some embodiments, said process achieves less than about 50 ppm 10-Br-carbamazepine relative to carbamazepine. In some embodiments, said process achieves less than about 40 ppm 10-Br-carbamazepine relative to carbamazepine. In some embodiments, said process achieves less than about 30 ppm 10-Br-carbamazepine relative to carbamazepine. In some embodiments, said process achieves less than about 20 ppm 10-Br-carbamazepine relative to carbamazepine. In some embodiments, said process achieves less than about 10 ppm 10-Br-carbamazepine relative to carbamazepine. In some embodiments, said composition comprises about 5-15 mg/mL carbamazepine, such as about 10 mg/mL carbamazepine. In some embodiments, said composition comprises about 200-300 mg/mL sulfobutylether-7-β-cyclodextrin sodium, such as about 250 mg/mL sulfobutylether-7-β-cyclodextrin sodium. In some embodiments, said composition is buffered, e.g., with a phosphate buffer, acetate buffer, or citrate buffer to achieve a pH between about 5.5 and 7.5, such as about 6.2. Buffering may be achieved, e.g., by addition of about 0.4-1.5 mg/ml, such as about 0.5-1.0 mg/mL, such as about 0.78 mg/mL sodium phosphate monobasic dihydrate to said composition and adjusting pH to about 6.2 using NaOH or HCl as required. In some embodiments, said composition is sterile.

In some embodiments, said composition comprises about 10 mg/mL carbamazepine, about 250 mg/mL sulfobutylether-7-β-cyclodextrin sodium, about 0.78 mg/mL sodium phosphate monobasic dihydrate, and water for injection, having pH about 6.2 and said carbamazepine is manufactured in a process that achieves less than about 60 ppm, such as less than about 50 ppm, such as less than about 40 ppm, such as less than about 30 ppm, such as less than about 20 ppm, or such as less than about 10 ppm 10-Br-carbamazepine relative to carbamazepine. In some embodiments, said composition comprises about 10 mg/mL carbamazepine, about 250 mg/mL sulfobutylether-7-β-cyclodextrin sodium, about 0.78 mg/mL sodium phosphate monobasic dihydrate, and water for injection, having pH about 6.2 and said carbamazepine is manufactured in a process that achieves less than about 60 ppm 10-Br-carbamazepine relative to carbamazepine. In some embodiments, said composition comprises about 10 mg/mL carbamazepine, about 250 mg/mL sulfobutylether-7-β-cyclodextrin sodium, about 0.78 mg/mL sodium phosphate monobasic dihydrate, and water for injection, having pH about 6.2 and said carbamazepine is manufactured in a process that achieves less than about 50 ppm 10-Br-carbamazepine relative to carbamazepine. In some embodiments, said composition comprises about 10 mg/mL carbamazepine, about 250 mg/mL sulfobutylether-7-β-cyclodextrin sodium, about 0.78 mg/mL sodium phosphate monobasic dihydrate, and water for injection, having pH about 6.2 and said carbamazepine is manufactured in a process that achieves less than about 40 ppm 10-Br-carbamazepine relative to carbamazepine. In some embodiments, said composition comprises about 10 mg/mL carbamazepine, about 250 mg/mL sulfobutylether-7-β-cyclodextrin sodium, about 0.78 mg/mL sodium phosphate monobasic dihydrate, and water for injection, having pH about 6.2 and said carbamazepine is manufactured in a process that achieves less than about 30 ppm 10-Br-carbamazepine relative to carbamazepine. In some embodiments, said composition comprises about 10 mg/mL carbamazepine, about 250 mg/mL sulfobutylether-7-β-cyclodextrin sodium, about 0.78 mg/mL sodium phosphate monobasic dihydrate, and water for injection, having pH about 6.2 and said carbamazepine is manufactured in a process that achieves less than about 20 ppm 10-Br-carbamazepine relative to carbamazepine. In some embodiments, said composition comprises about 10 mg/mL carbamazepine, about 250 mg/mL sulfobutylether-7-β-cyclodextrin sodium, about 0.78 mg/mL sodium phosphate monobasic dihydrate, and water for injection, having pH about 6.2 and said carbamazepine is manufactured in a process that achieves less than about 10 ppm 10-Br-carbamazepine relative to carbamazepine.

In some embodiments, said carbamazepine is manufactured in a process comprising a chemical reaction as depicted in (i), (*J. Org. Chem.*, 44, 497-501, 1979; hereby incorporated by reference in its entirety):

In some embodiments, said carbamazepine is manufactured in a process comprising a chemical reaction depicted in (ii), (*Org. Lett.*, 13, 5592-5595, 2011; *Tetrahedron*, 51, 2091-2098, 1995; each hereby incorporated by reference in its entirety):

In some embodiments, said carbamazepine is manufactured in a process comprising a chemical reaction depicted in (iii), (*Org. Lett.*, 13, 5592-5595, 2011; hereby incorporated by reference in its entirety):

In some embodiments, said carbamazepine is manufactured in a process comprising a catalytic dehydrogenation reaction depicted in (iv), (*J. Org. Chem.*, 26, 135-138, 1961; *Chem. Pharm. Bull.*, 30, 24-27, 1982; EP237952; each hereby incorporated by reference in its entirety):

In some embodiments, said carbamazepine is manufactured in a process comprising dehydrogenation with sulphur as depicted in (v), (*Chem. Berichte*, 93, 392-399, 1960; hereby incorporated by reference in its entirety):

In the above-depicted carbamazepine manufacturing processes, R is included to account for the fact that the carbamoyl group of carbamazepine (—C(=O)NH$_2$) may be added to the ring system before or after the formation of the double bond. In one embodiment, R is selected from H, carbamoyl, a protecting group, such as alkyl (methyl, ethyl or propyl), aryl, such as phenyl, or —C(O)CH$_3$, or a group that may be transformed into carbamoyl, such as —C(=O) Cl. Thus, in some embodiments, said carbamazepine is manufactured in a process that achieves essentially no 10-Br-carbamazepine, wherein the process comprises a chemical reaction from the group consisting of (i)-(iv)

above, wherein R is H, carbamoyl, a protecting group, or a group that may be transformed to carbamoyl. In some embodiments, said process comprises the chemical reaction wherein R is H, carbamoyl, a protecting group, or a group that may be transformed to carbamoyl. In some embodiments, said process achieves less than about 60 ppm 10-Br-carbamazepine relative to carbamazepine.

In still another aspect, the invention provides a method for the treatment of a disease in a patient in need thereof selected from the group consisting of seizures, mania, bipolar depression, mixed episodes, major depressive disorder, and trigeminal neuralgia, said method comprising the administration of a therapeutically effective amount of an injectable pharmaceutical composition of the present invention to a patient in need thereof. In some embodiments, the method comprises the administration of a therapeutically effective amount of a composition comprising carbamazepine and sulfobutylether-7-β-cyclodextrin, wherein said composition is essentially free of 10-Br-carbamazepine. In some embodiments, said 10-Br-carbamazepine is present in an amount less than about 60 ppm relative to carbamazepine. In some embodiments, said 10-Br carbamazepine is present in an amount between about 1 and about 60 ppm relative to carbamazepine. In some embodiments, said administration occurs over a period from about 5 to about 60 minutes, such as about 30 minutes. In some embodiments, administration occurs intravenously. In some embodiments, the composition comprises about 10 mg/mL carbamazepine and about 25% w/v sulfobutylether-7-β-cyclodextrin, and wherein the composition is administered intravenously.

In still another aspect, the invention provides the use of an injectable pharmaceutical composition of the present invention in the manufacture of a medicament for the treatment of a disease selected from the group consisting of seizures, mania, bipolar depression, mixed episodes, major depressive disorder, and trigeminal neuralgia.

In still another aspect, the invention provides an injectable pharmaceutical composition of the present invention for use in the treatment of a disease selected from the group consisting of seizures, mania, bipolar depression, mixed episodes, major depressive disorder, and trigeminal neuralgia. In some embodiments, said seizure is selected from:
   partial seizures with complex symptomatology,
   generalized tonic-clonic seizures, or
   mixed seizure patterns which include the above, or other partial or generalized seizures.
Thus, in some embodiments, said patient has partial seizures with complex symptomatology. In some embodiments, said patient has generalized tonic-clonic seizures. In some embodiments, said patient has mixed seizures patterns.

In some embodiments, said disease is selected from acute mania or mixed episode, including severe or psychotic mania or treatment resistant mania.

In some embodiments, said disease is selected from acute or severe or suicidal major depressive disorder or from acute or severe or suicidal bipolar depression.

In some embodiments, said disease is selected from treatment resistant major depressive disorder or treatment resistant bipolar depression.

In the present context, the term "therapeutically effective amount" of a pharmaceutical composition means an amount sufficient to alleviate, arrest, partially arrest, remove, or delay the clinical manifestations of a given disease and its complications in a therapeutic intervention comprising the administration of said compound. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

In the present context, "treatment" or "treating" is intended to indicate the management and care of a patient for the purpose of alleviating, arresting, partly arresting, removing, or delaying progress of the clinical manifestation of the disease.

In one embodiment, the injectable pharmaceutical composition of the present invention is administered at about 200-1500 mg carbamazepine/day, such as about 280-1120 mg carbamazepine/day. An injectable pharmaceutical composition of the present invention may be diluted prior to administration, which is conveniently done by infusion intravenously over, e.g., about 30 minutes. Dilution may be affected, e.g., by 0.9% NaCl, lactated Ringer's solution, or 5% dextrose.

In some embodiments, the patient intended to receive the injectable pharmaceutical composition of the present invention was previously administered carbamazepine orally and is temporarily unable to have carbamazepine administered orally, i.e., the injectable pharmaceutical composition of the present invention is for replacement therapy for oral carbamazepine formulation. In this embodiment, the daily dose of an injectable pharmaceutical composition of the present invention is about 30-100%, such as about 65-75%, or such as about 70% of the total daily dose of oral carbamazepine. In one embodiment, an injectable pharmaceutical composition of the present invention is administered multiple times during the day, such as four times separated by about six hours. In some embodiments, said administration occurs over a period from about 5 to about 60 minutes, such as about 30 minutes.

In some embodiments, an injectable pharmaceutical composition of the present invention comprises about 10 mg/mL of carbamazepine, about 25% weight/volume of sulfobutylether-7-β-cyclodextrin, and a physiologically acceptable fluid, wherein said composition is administered intravenously, and contains carbamazepine in a dose of about 30% to about 100% of a human's oral maintenance dose, and wherein said composition is essentially free of 10-Br-carbamazepine. In some embodiments, said composition contains carbamazepine in a dose of about 65% to about 75% of the human's oral maintenance dose.

The injectable pharmaceutical composition of the present invention may also be useful in achieving a therapeutically relevant plasma level of carbamazepine fast which is expected to also provide a fast onset of a clinical effect. This may be particularly useful, e.g., in the treatment of acute mania. In some embodiments, the injectable pharmaceutical composition of the present invention may achieve a therapeutically relevant plasma level of carbamazepine within 30 minutes. See, e.g., data disclosed in U.S. Pat. Nos. 9,629,797 and 9,770,407 (each hereby incorporated by reference in its entirety).

Data disclosed in, e.g., U.S. Pat. No. 6,629,797 (hereby incorporated by reference in its entirety) show that the average oral bioavailability for carbamazepine is 65-70%. This may also be used to guide dosages for carbamazepine naïve patients.

All references, including publications, patent applications, and patents, cited herein are hereby incorporated by reference in their entirety and to the same extent as if each reference were individually and specifically indicated to be incorporated by reference and were set forth in its entirety herein, regardless of any separately provided incorporation of particular documents made elsewhere herein.

The use of the terms "a", "an", and "the" and similar referents in the context of describing the invention are to be construed to cover both the singular and the plural, unless otherwise indicated herein or clearly contradicted by context. For example, the phrase "the composition" is to be understood as referring to various compositions of the invention or a particular described aspect, unless otherwise indicated.

The invention can be described by way of the following Examples, which are presented for example only and not intended to limit the scope of the invention as described in other embodiments.

EXAMPLES

Example 1

Three batches of vials of an injectable pharmaceutical composition comprising carbamazepine and sulfobutylether-7-β-cyclodextrin from a single carbamazepine batch were prepared. Carbamazepine, sulfobutylether-7-β-cyclodextrin sodium (betadex), phosphate monobasic dihydrate, and water for injection were mixed and pH adjusted to 6.2. The solutions were sterile filtered through three 0.2 μm filters and filled in vials (20 mL) which were terminally sterilized by autoclaving at 130° C. The batches were manufactured at commercial scale (approximately 1000 L) under good manufacturing practice ("GMP") and standard environmental conditions for pharmaceutical production. Each batch of vials contained 10 mg/mL carbamazepine, 250 mg/mL sulfobutylether-7-β-cyclodextrin sodium, 0.78 mg/mL sodium phosphate monobasic dihydrate, and water for injection at pH 6.2.

Vials from each batch were analyzed for particulates after three months of storage in upright and inverted positions at conditions indicated in Table 1 below. The analyses were carried in an ISO 14644 Class 5 clean room facility.

TABLE 1

| | Storage conditions. | | | |
|---|---|---|---|---|
| | Storage conditions | | | |
| | 25° C./60% RH | | 40° C./75% RH | |
| Batch No. | Upright | Inverted | Upright | Inverted |
| 75 | ✓ | ✓ | | |
| 76 | ✓ | ✓ | ✓ | ✓ |
| 77 | ✓ | ✓ | ✓ | ✓ |

Figure 2:
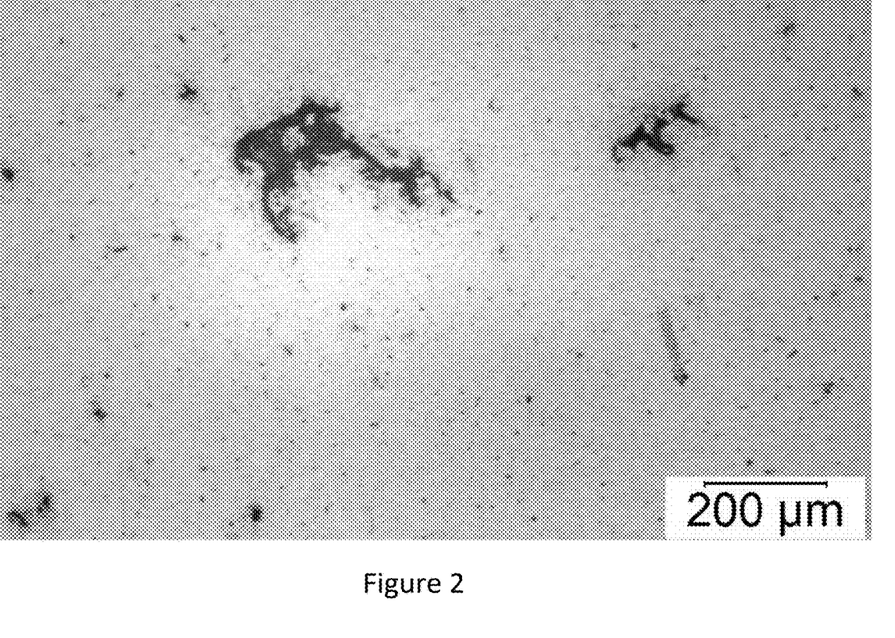
FIG. 2: Stereomicroscope image of particulates isolated from a batch of Carnexiv™.
Figure 3:
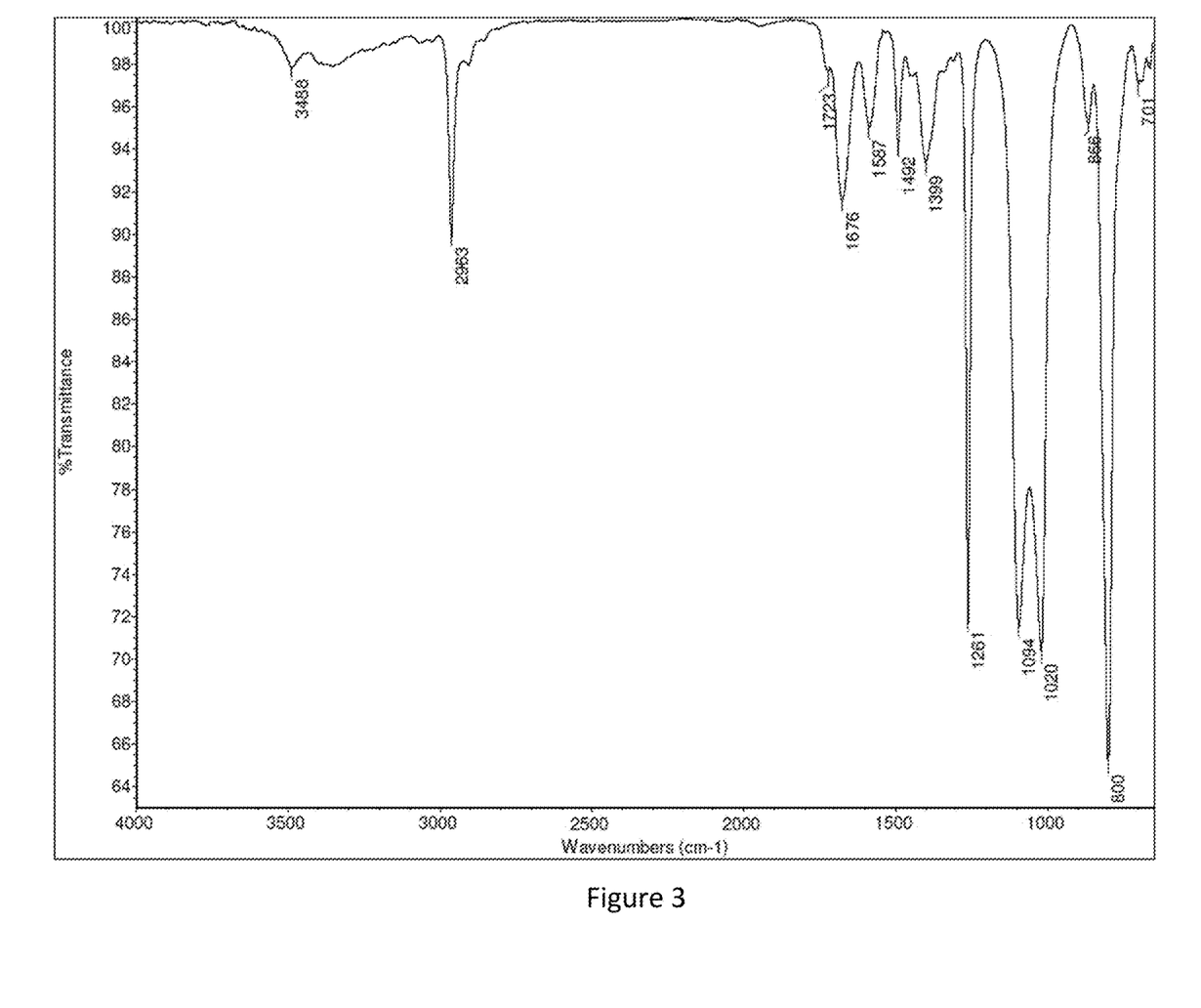
FIG. 3: Infrared spectrum of particulates isolated from a batch of Carnexiv™ after three months of storage.
Figure 4:
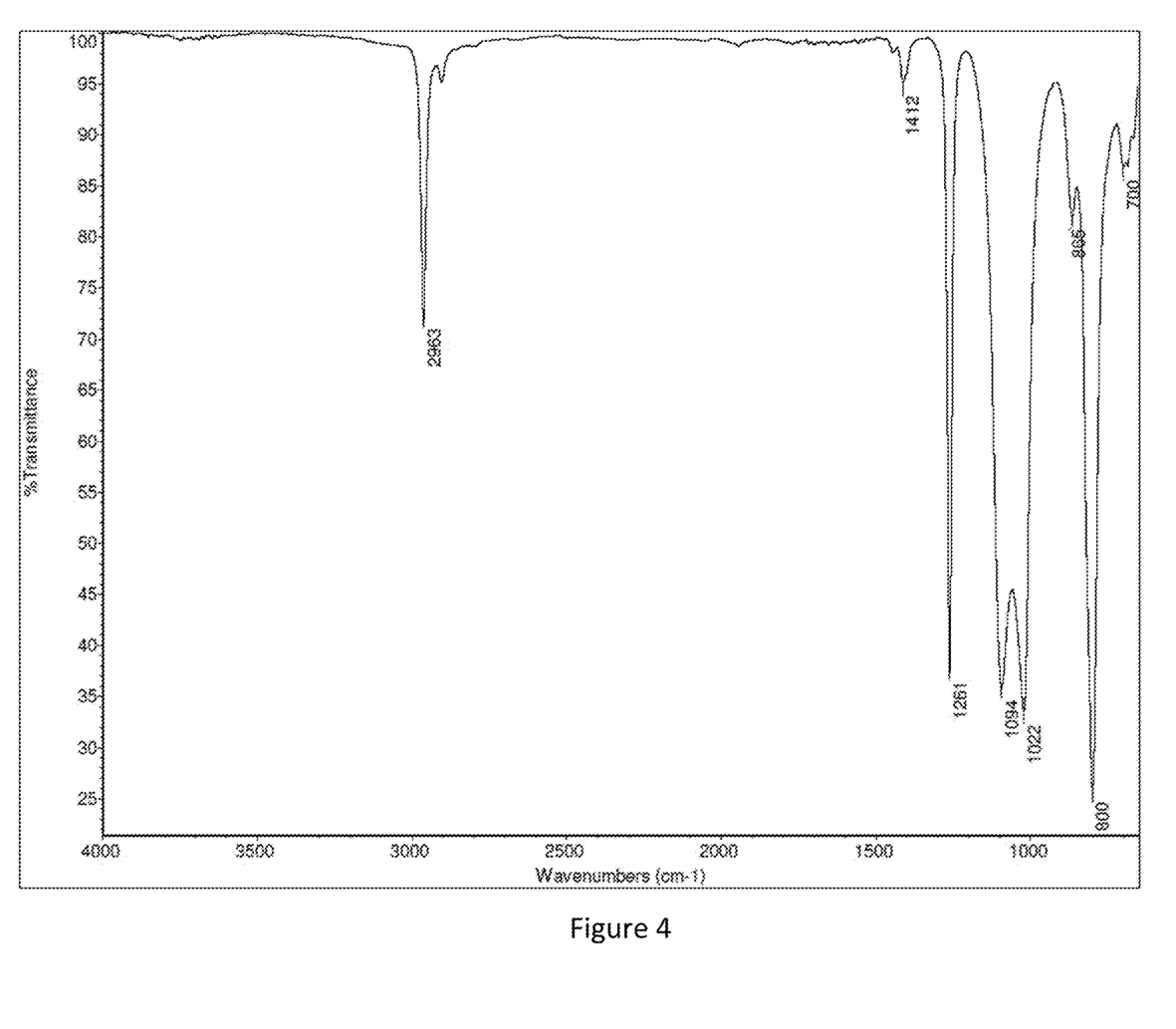
FIG. 4: Infrared spectrum of carbamazepine.
Figure 5:
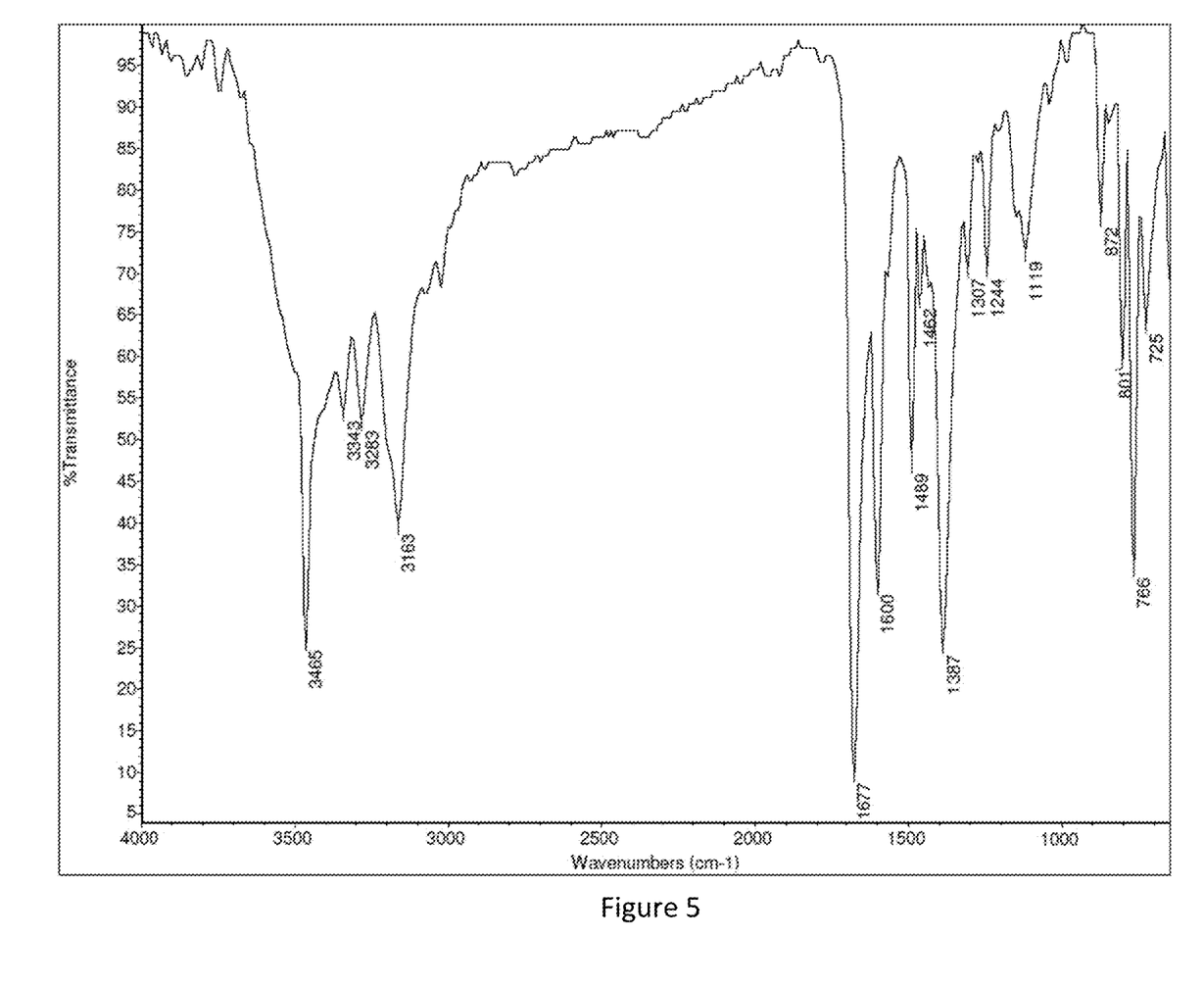
FIG. 5: Infrared spectrum of silicon oil.

Vials from all batches and all storage conditions contained visible particulates. Using a low magnification stereomicroscope, it was established that vials from all batches and storage conditions contained comparable amounts of colourless, stingy, amorphous particulates. Particulates from batch 75 upright and inverted were isolated on a 0.8 μm filter. Stereomicroscope analyses revealed particulates of less than approximately 400 μm (see FIG. 2). The same particulates were pressed on a KBr tablet and analyzed using micro-Fourier transform IR spectroscopy in transition mode. The IR spectra obtained from particulates from the two batches are essentially similar, and that obtained from batch 75 upright is shown in FIG. 3. The peaks are indicative of the presence of silicon oil and a carbamazepine analogue—see reference IR spectra for silicon oil and carbamazepine in FIGS. 4 and 5, respectively.

Portions of the particles isolated from batch 75 upright and inverted were mounted on a beryllium substrate for elemental analysis using SEM/EDS. The particulates consist of carbon, oxygen, silicon (consistent with silicon oil), nitrogen (consistent with carbamazepine analogue), and elevated levels of bromine. Table 2 below depicts representative SEM/EDS data for three isolated particulates.

TABLE 2

| Elemental analysis in isolated particulates from batch 75, 3 months storage (weight %). | | | |
|---|---|---|---|
| Element | Particle 1 | Particle 2 | Particle 3 |
| C | 65.05 | 63.42 | 63.35 |
| N | 4.43 | 4.52 | 4.37 |
| O | 13.45 | 13.53 | 14.45 |
| Si | 8.92 | 10.89 | 10.56 |
| Br | 8.16 | 7.63 | 7.27 |
| Total | 100 | 100 | 100 |

Figure 6:
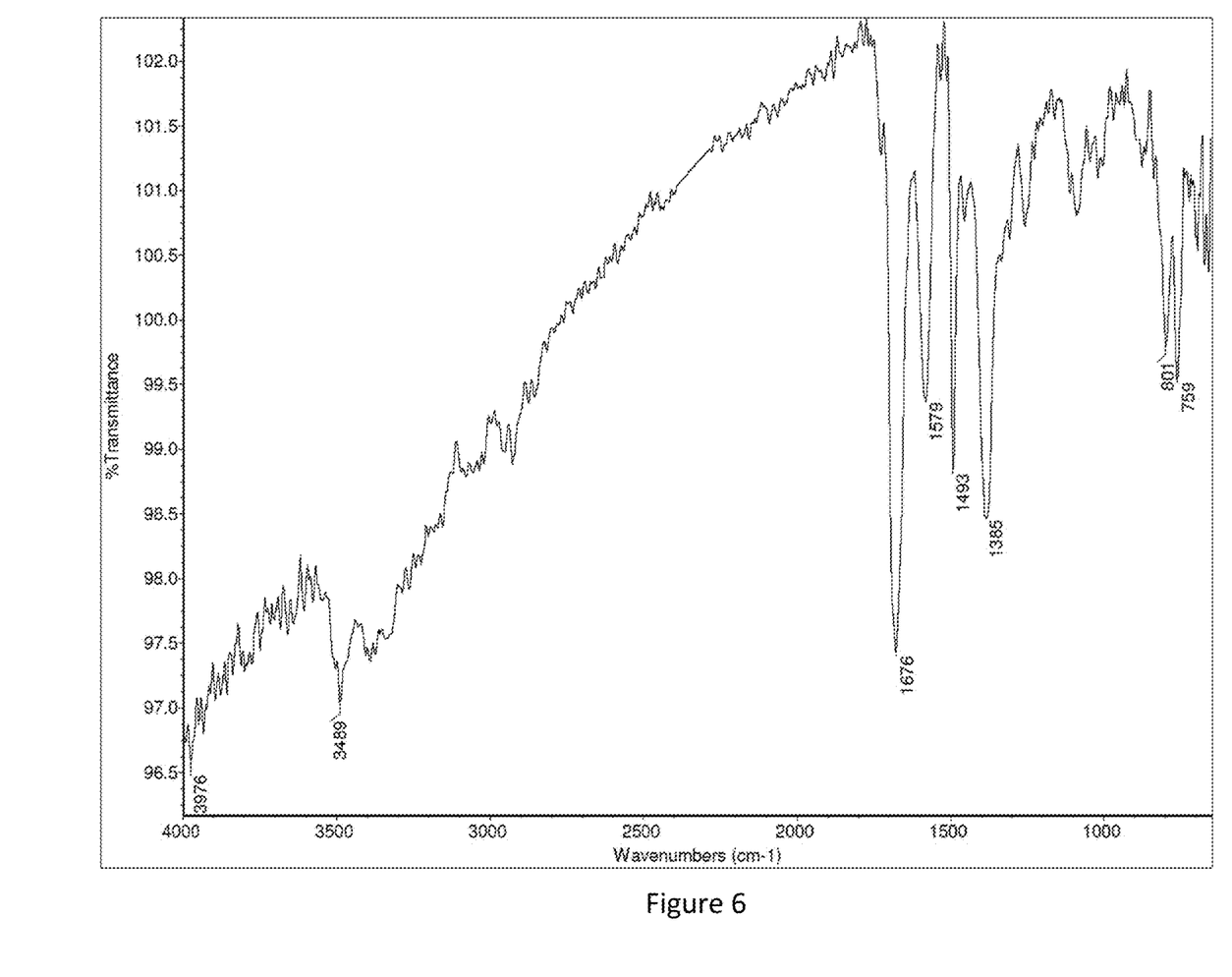
FIG. 6: Infrared spectrum of particulates isolated from a batch of Carnexiv™ after three months of storage, rinsed with nonane.

Particulates from batch 77 upright 25° C. were isolated and prepared for IR analysis as described above. Prior to mounting the particulates on the KBr tablet they were rinsed with nonane to remove silicon. The IR spectrum is shown in FIG. 6, which lends additional support to the notion that the particulate comprises a carbamazepine analogue.

SEM/EDS analysis of the rubber stoppers of the vials shows no traces of bromine.

The silicon oil identified is likely to originate from raw materials or production equipment.

Example 2

Vials from batch 75 were analyzed essentially as described in Example 1 after 12 months of storage at 25° C./60% RH. The IR spectrum is shown in FIG. 6 and is essentially similar to that obtained after three months of storage (FIG. 3). SEM/EDS data for particulate isolated is shown in Table 3 below.

TABLE 3

| Elemental analysis in isolated particulates from batch 75, 12 months storage (weight %). | |
|---|---|
| Element | Weight % |
| C | 56.42 |
| N | 4.17 |
| O | 24.76 |
| Si | 11.19 |
| Cl | 0.10 |
| Br | 3.36 |
| Total | 100 |

The data obtained in Example 2 confirms the conclusions drawn based on the data obtained in Example 1, i.e., that the particulates comprise a bromine-containing carbamazepine analogue.

Example 3

Chromatographic Assay for 10-Br-carbamazepine Analysis

Column: 50 mm×2.1 mm with propyl cyano bonded 1.8 μm column material (Acquity HSS CN). Flow rate 0.4 mL/min. Temperature 40° C. MS detection at m/z 316.9 (determined by an analytical standard). Mobile phase A: H$_2$O:HCOOH 2000:1. Mobile phase B: MeOH:HCOOH 2000:1.

Approximately 100 mg sample was dissolved in 10 mL MeOH and further diluted with water to 20 mL. Results were calculated relative to a standard of 10-bromo carbamazepine in the concentration range 0.1 to 5 μg/mL and the nominal amount of carbamazepine.

| Batch No. | 10-Br-carbamazepine (ppm relative to carbamazepine) |
|---|---|
| 75 | 64.6 |
| 76 | 81.4 |
| 77 | 70.2 |

The batch of carbamazepine used for the manufacture of the vials analyzed in Example 4 was synthesized as depicted below.

| Gradient | | |
|---|---|---|
| Time (min) | % A | % B |
| 0 | 80 | 20 |
| 1.0 | 80 | 20 |
| 8.0 | 45 | 55 |
| 9.0 | 45 | 55 |
| 9.1 | 80 | 20 |

The batch of carbamazepine used for the manufacture of the vials analyzed in Examples 1 and 2 was analyzed using the above chromatographic assay. The batch was found to contain 81.5 ppm 10-Br-carbamazepine relative to carbamazepine.

Batches 75, 76, and 77 analyzed in Examples 1 and 2 were analyzed for 10-Br-carbamazepine content, and the table below depicts the results.

The batch is, therefore, expected to be essentially free of 10-Br-carbamazepine. This was confirmed in analysis using the above chromatographic assay.

Example 4

A new batch of vials of an injectable pharmaceutical composition comprising carbamazepine and sulfobutylether-7-β-cyclodextrin was prepared using the batch of carbamazepine shown in Example 3 to be essentially free of 10-Br carbamazepine, i.e., the batch was prepared as depicted in the scheme above. The batch of vials was prepared as described in Example 1 with the notable difference that preparation took place in a non-sterile development laboratory.

Electron microscope analysis of vials immediately after manufacturing revealed no colorless, stingy, amorphous particulates. Some particles were found but they were identified as environmental debris owing to the fact that the vials were not manufactured under standard environmental requirements for pharmaceutical production. SEM/EDS analysis of these particles also failed to show the presence of bromine.

Following 3 months of storage at 25° C./60% RH and 40° C./75% RH, the vials were re-analyzed for particulates. The data confirmed the analyses made immediately after the preparation of the vials, i.e., no colorless, stingy, amorphous particulates.

Example 5

Two batches of vials of an injectable pharmaceutical composition comprising carbamazepine and sulfobutylether-7-β-cyclodextrin from a single carbamazepine batch were prepared. Carbamazepine, sulfobutylether-7-β-cyclodextrin sodium (betadex), phosphate monobasic dihydrate, and water for injection were mixed and the pH adjusted to 6.2. The solutions were sterile filtered through three 0.2 μm filters and filled in vials (20 mL) which were terminally sterilized by autoclaving at 130° C. The batches were manufactured at commercial scale (approximately 1000 L) under standard environmental conditions for pharmaceutical production. Each batch of vials contained 10 mg/mL carbamazepine, 250 mg/mL sulfobutylether-7-β-cyclodextrin sodium, 0.78 mg/mL sodium phosphate monobasic dihydrate, and water for injection at pH 6.2.

The carbamazepine used to prepare to the batches of Carnexiv™ in this example was manufactured in the same way as the carbamazepine used in Example 4 and is essentially free of 10-Br-carbamazepine.

Vials from each batch were analyzed for particulates after 3 months of storage in upright and inverted positions at conditions indicated in Table 4 below.

TABLE A

| | Storage conditions. | | | |
| --- | --- | --- | --- | --- |
| | Storage conditions | | | |
| | 25° C./60% RH | | 40° C./75% RH | |
| Batch No. | Upright | Inverted | Upright | Inverted |
| 21 | ✓ | ✓ | ✓ | ✓ |
| 22 | ✓ | ✓ | ✓ | ✓ |

✓ indicates that the vial is clear and free of visible particulates after 3 months storage.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and rearranged in various ways within the scope and spirit of the invention.

The invention claimed is:

1. An injectable pharmaceutical composition comprising carbamazepine and a sulfobutylether-7-β-cyclodextrin, wherein said composition comprises less than about 60 ppm 10-Br-carbamazepine relative to carbamazepine.

2. The composition according to claim 1, wherein the composition comprises about 10 mg/mL carbamazepine and about 250 mg/mL sulfobutylether-7-β-cyclodextrin, wherein the sulfobutylether-7-β-cyclodextrin is sulfobutylether-7-β-cyclodextrin sodium.

3. The composition according to claim 2, wherein the composition further comprises about 0.78 mg/mL sodium phosphate monobasic dihydrate and water, the composition having about 6.2.

4. The composition according to claim 1 comprising
a) about 10 mg/mL of carbamazepine,
b) about 25% weight/volume of sulfobutylether-7-β-cyclodextrin, and further comprising
c) a physiologically acceptable fluid,
wherein said composition is administered intravenously, and contains carbamazepine in a dose of about 30% to about 100% of a human's oral maintenance dose.

5. The composition according to claim 4, wherein said composition contains carbamazepine in a dose of about 65% to about 75% of the human's oral maintenance dose.

6. The composition according to claim 1, wherein said carbamazepine is manufactured in a process that achieves less than about 60 ppm 10-Br-carbamazepine relative to carbamazepine, wherein the process comprises a chemical reaction selected from the group consisting of -continued Pd/C in vacuo, Mn₂O₃, SnO₂, Fe₂O₃, or Cr₂O₃ → (iv)

, and

Sulphur → (v)

, wherein R is H, carbamoyl, a protecting group, or a group that may be transformed to carbamoyl.

7. The composition according to claim 6, wherein said process comprises the chemical reaction Sulphur →

, wherein R is H, carbamoyl, a protecting group, or a group that may be transformed to carbamoyl.

8. The composition according to claim 6, wherein the composition comprises about 10 mg/mL, carbamazepine and about 250 mg/mL, sulfobutylether-7-β-cyclodextrin, wherein the sulfobutylether-7-β-cyclodextrin is sulfobutylether-7-β-cyclodextrin sodium.

9. The composition according to claim 8, wherein the composition further comprises about 0.78 mg/mL, sodium phosphate monobasic dihydrate and water, the composition having pH about 6.2.

10. The composition according to claim 1, wherein the composition comprises less than about 30 ppm 10-Br-carbamazepine relative to carbamazepine.

11. The composition according to claim 10, wherein the composition comprises less than about 10 ppm 10-Br-carbamazepine relative to carbamazepine.

12. The composition according to claim 2, wherein the composition comprises less than about 30 ppm 10-Br-carbamazepine relative to carbamazepine.

13. The composition according to claim 12, wherein the composition comprises less than about 10 ppm 10-Br-carbamazepine relative to carbamazepine.

14. The composition according to claim 4, wherein the composition comprises less than about 30 ppm 10-Br-carbamazepine relative to carbamazepine.

15. The composition according to claim 14, wherein the composition comprises less than about 10 ppm 10-Br-carbamazepine relative to carbamazepine.

16. The composition according to claim 5, wherein the composition comprises less than about 30 ppm 10-Br-carbamazepine relative to carbamazepine.

17. The composition according to claim 16, wherein the composition comprises less than about 10 ppm 10-Br-carbamazepine relative to carbamazepine.

18. The composition according to claim 8, wherein the composition comprises less than about 30 ppm 10-Br-carbamazepine relative to carbamazepine.

19. The composition according to claim 18, wherein the composition comprises less than about 10 ppm 10-Br-carbamazepine relative to carbamazepine.

* * * * *

UNITED STATES PATENT AND TRADEMARK OFFICE
CERTIFICATE OF CORRECTION

PATENT NO. : 11,529,357 B2
APPLICATION NO. : 16/778302
DATED : December 20, 2022
INVENTOR(S) : Hans Petersen et al.

It is certified that error appears in the above-identified patent and that said Letters Patent is hereby corrected as shown below:

In the Claims

At Column 24, Claim number 8, Line numbers 4-5, should read:
8. The composition according to claim 6, wherein the composition comprises about 10 mg/mL carbamazepine and about 250 mg/mL sulfobutylether-7-β-cyclodextrin, wherein the sulfobutylether-7-β-cyclodextrin is sulfobutylether-7-β-cyclodextrin sodium.

At Column 24, Claim number 9, Line number 9, should read:
9. The composition according to claim 8, wherein the composition further comprises about 0.78 mg/mL sodium phosphate monobasic dihydrate and water, the composition having pH about 6.2.

Signed and Sealed this
Twenty-eighth Day of February, 2023

Katherine Kelly Vidal
*Director of the United States Patent and Trademark Office*